United States Patent [19]

Neti et al.

[11] 4,455,213
[45] Jun. 19, 1984

[54] PRESSURE EQUALIZATION SYSTEM FOR MEMBRANE TYPE AMPEROMETRIC SENSORS

[75] Inventors: Radhakrishna M. Neti, Brea; Kenneth B. Sawa, Yorba Linda, both of Calif.

[73] Assignee: Beckman Instruments, Inc., Fullerton, Calif.

[21] Appl. No.: 221,143

[22] Filed: Dec. 29, 1980

[51] Int. Cl.³ ............................................. G01N 27/46
[52] U.S. Cl. ...................................... 204/415; 204/1 T
[58] Field of Search ................ 204/1 P, 195 P, 195 R; 73/747

[56] References Cited

U.S. PATENT DOCUMENTS

| | | | |
|---|---|---|---|
| 116,176 | 6/1871 | Gerner | 73/747 |
| 3,208,928 | 9/1965 | Landers et al. | 204/195 F |
| 3,367,849 | 2/1968 | Blaedel et al. | 23/230 B |
| 3,510,421 | 5/1970 | Gealt | 204/195 |
| 3,551,315 | 12/1970 | Friconneau et al. | 204/195 G |
| 3,577,332 | 5/1971 | Porter et al. | 204/195 |
| 3,929,603 | 12/1975 | Porter | 204/195 P |
| 4,092,232 | 5/1978 | Zetter | 204/195 P |
| 4,126,531 | 11/1978 | Porter et al. | 204/195 P |
| 4,178,223 | 12/1979 | Ohashi et al. | 204/195 P |
| 4,268,370 | 5/1981 | Neti | 204/1 P |

Primary Examiner—T. Tung
Attorney, Agent, or Firm—R. J. Steinmeyer; P. R. Harder; E. C. Jason

[57] ABSTRACT

A membrane type amperometric gas sensor is provided with a pressure equalization passage between the exterior and interior of the cell in which the electrodes are located. Cell fluids move into and out of the passage as necessary to maintain the pressure inside the cell substantially equal to the pressure outside the cell over a wide range of pressures and temperatures. A movable fluid plug or seal located in the passage protects the fluids inside of the cell from contact with the gas being sensed and from the atmosphere for all permissible values of pressure and temperature.

27 Claims, 8 Drawing Figures

PRESSURE EQUALIZATION SYSTEM FOR MEMBRANE TYPE AMPEROMETRIC SENSORS

BACKGROUND OF THE INVENTION

Amperometric gas sensors typically include an electrolytic cell having a pair of electrodes which are immersed in an electrolyte solution and which are exposed to the gas to be measured through a gas permeable membrane. Because of the thinness of the membrane, the cell is sensitive to differences in the pressure between the inside and outside of the cell. As a result, the need for providing a pressure compensation mechanism has long been recognized. One group of approaches to solving this problem is described in U.S. Pat. No. 4,126,531, issued on Nov. 21, 1978, entitled "Sensor With Annular Pressure Compensating Means" and in U.S. Pat. No. 3,577,332, issued on May 4, 1971, entitled "Polarographic Cell." In the former patent, a pressure compensating membrane serves as an elastic compensating cover for a plurality of pressure compensating openings. In the latter patent a movable diaphragm transmits external pressure changes to the interior of the cell by flexing in the manner of a barometer and thereby increasing or decreasing the pressure within the cell. While such approaches may work well in the presence of relatively small changes in pressure, they cannot deal with large pressure changes such as, for example, changes which amount to a substantial percentage of atmospheric pressure.

Other approaches shown, for example, in U.S. Pat. No. 3,510,421, issued on May 5, 1970, entitled "Polarographic Cell" and U.S. Pat. No. 3,929,603, issued on Dec. 30, 1975, entitled "Electrolytic Sensor with Pressure Compensating Means," involve the use of internal or external pressure compensating bladders having substantially fixed volumes. While such structures provide a degree of compensation for changes in the pressure of gases exterior to the cell, they are poorly equipped to deal with changes in pressure resulting from changes in the interior of the cell, such as those that are incident to the thermal expansion and contraction of the cell and its contents.

Still another approach to the solution of the pressure compensation problem is shown in U.S. Pat. No. 4,178,223, issued on Dec. 11, 1979, entitled "Electrical Oxygen Probe." In this patent the interior of the cell is simply left open to the atmosphere. While such an approach no doubt prevents the build up of pressure differences, it has the disadvantage that, being unsealed, contaminants can enter through the vents to pollute the electrolyte solution. In addition, the electrolyte can change in concentration as a result of evaporation and thereby produce inaccurate readings.

SUMMARY OF THE INVENTION

In accordance with the present invention, the above described problems and shortcomings are avoided by providing a pressure and temperature compensating passage whereby pressure is directly communicated between the exterior and interior of the cell, without providing a path through which external gases may enter the cell or a path through which internal fluids may leave the cell. As a result, the electrode of the present invention is pressure compensated and yet is protected both from the contamination incident to the entry of a sample gas stream or ambient air and from the evaporation of fluids from the interior of the cell.

In the preferred embodiment the above objectives are accomplished by providing, in the compensating passage, a movable fluid plug or barrier or seal which maintains the separation of the fluids inside and outside of the cell in spite of the movement of cell fluids from the cell into the passage and vice versa in the course of the pressure equalization process. More particularly, the fluid plug moves toward the exterior end of the passage when the pressure inside the cell is greater than the pressure outside of the cell and moves inwardly toward the interior end of the passage when the pressure inside of the cell is less than the pressure outside of the cell. Because the fluid plug comes to rest only when the pressures applied to the two surfaces thereof are equal, and because the fluid plug has a very low mass and low frictional resistance to movement, its movement is a highly sensitive and rapidly acting means of equalizing the interior and exterior pressures of the cell.

In accordance with another feature of the present invention, the pressure compensating passage is provided with a volume substantially in excess of that which would be needed in a mere conduit that connected the interior and exteriof of the cell. This allows the passage to serve a storage or reservoir function by allowing substantial quantities of the cell fluids to be drawn from or added to the cell, as necessary to establish pressure equilization, without forcing the seal out of either end of the passage. At a minimum, the volume of the reservoir should be sufficient to receive any additional cell fluids, or to supply any deficiency in cell fluids that result from the thermal expansion and contraction of the cell and its contents over the maximum permissible range of electrode temperatures. Still further reservoir capacity may, however, be desirable if the electrode cell of the invention is to operate in a configuration in which the electrode is partly filled with electrolyte and partly filled with a gas.

Whether the pressure compensating passage/reservoir is filled entirely with electrolyte, entirely with gas, or partly with electrolyte and partly with gas, however, it performs the fluid pressure transmission function contemplated by the present invention. In addition, any of such configurations accommodates pressure changes incident to thermal changes in the volume of the cell and its contents. Under all possible combinations of conditions, the movable fluid plug or barrier of the present invention protects the cell from contamination by external gases and from the evaporation of cell fluids.

Other objects and advantages of the present invention will be apparent from the following description of the preferred embodiments, when considered in conjunction with the following drawings.

DESCRIPTION OF THE PREFERRED EMBODIMENTS

Figure 1:
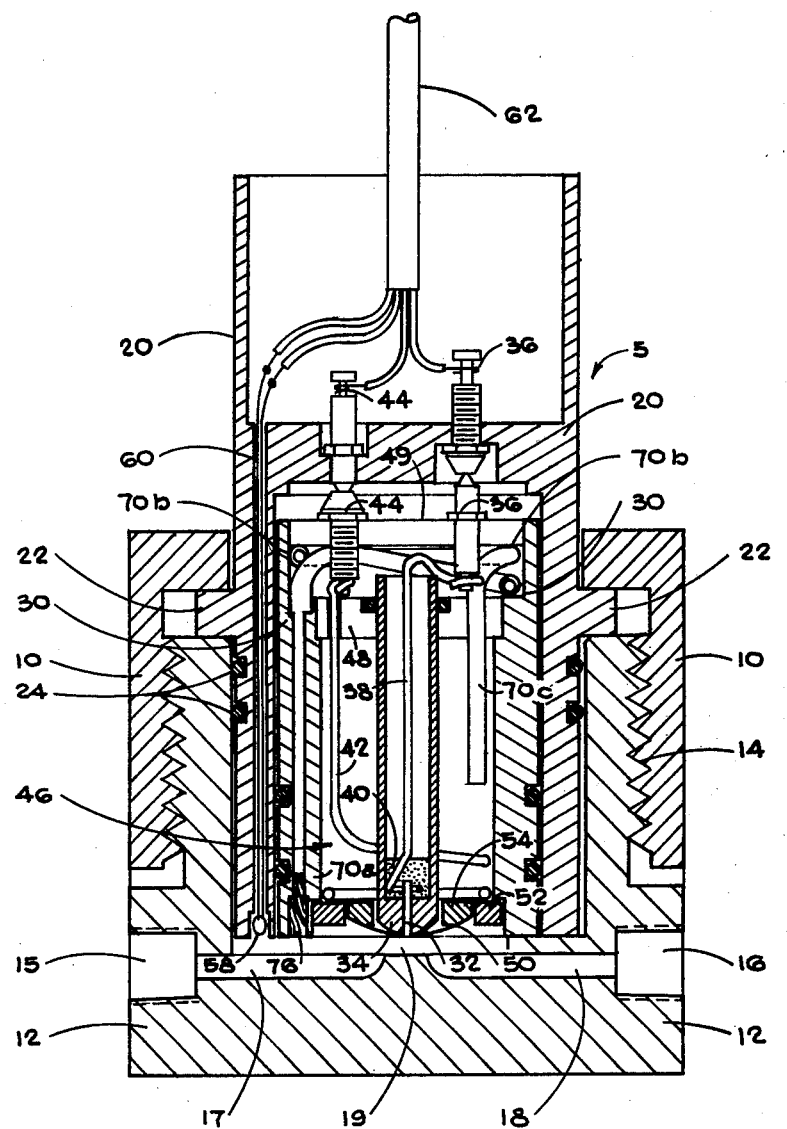
FIG. 1 is a cross-sectional view of a complete electrode assembly constructed in accordance with one embodiment of the present invention.

Referring to FIG. 1, there is shown a cross-sectional view of a complete gas sensor electrode assembly 5 constructed in accordance with one embodiment of the present invention. Electrode assembly 5 includes upper and lower housing sections 10 and 12, respectively, which may be generally cylindrical in shape and which may be made of a suitable plastic such as polyvinylidene fluoride. Housing sections 10 and 12 are held together by threads 14 and serve to support an electrode cell holder 20 which may also be generally cylindrical in shape. Electrode holder 20 is held in place between housing sections 10 and 12 by means of a suitable flange 22. The contact between housing sections 10 and 12 and cell holder 20 may be made substantially gas tight by means of suitable 0-rings 24.

Measurements of the concentration of sample gases such as, for example, oxygen are made by measuring the current flow through an electrolytic cell assembly 30 which fits snugly within cell holder 20. Cell 30 includes a cathode electrode 32, which is sealed in the end of a round ended glass tube 34 and which is connected to a cathode terminal post 36 through a conductor 38. Cathode 32 is preferably connected to conductor 38 through a bridge 40 of an electrically conductive epoxy cement.

Cell 30 also includes an anode electrode 42 which here takes the form of a coil of wire connected between an anode terminal post 44 and the interior periphery of electrolyte chamber 46. The latter chamber ordinarily contains an electrolyte such as, for example, a mild aqueous solution of potassium chloride and potassium hydroxide. This electrolyte establishes between cathode 32 and anode 42 a conductive path the conductivity of which varies with the concentration of the gas that is to be measured.

One end of cell 30 is closed by a nonconductive end plate or member 48 having air tight openings through which glass envelope 34 and conductor 42 are passed. The opposite end of cell 30 is closed by a suitable gas permeable membrane 50 which may, for example, comprise a one half mil sheet of fluorinated ethylene propylene. Membrane 50 is held in sealing relationship to the cell by the compression fit of locking rings 52 and 54 into the end of cell 30; these rings may be made of polyvinyl chloride. In operation, membrane 50 provides a liquid impermeable path whereby a sample gas may diffuse into cell 30 and thereby affect the current flow between cathode 32 and anode 42.

The sample gas to be measured is applied to membrane 50 through a sample gas passage in lower housing member 12. This gas passage includes a sample gas inlet 15 and a sample gas outlet 16 which are connected through conduits 17 and 18 and a sample gas chamber 19. Since chamber 19 has a volume which is relatively large in comparison with the cross-sectional area of conduits 17 and 18, the sample gas stream moves through chamber 19 at a relatively low speed, thereby minimizing the dynamic pressure effects that would occur if the gas stream were applied to membrane 50 in a high speed jet.

Because the foregoing structures and the purposes thereof are well known to those skilled in the art, the details of the structure and operation thereof will not be further described herein, except to the extent necessary to meaningfully describe the present invention.

In the event that the temperature as well as the concentration of the sample gas is to be continuously monitored, the electrode structure of FIG. 1 may be provided with a suitable temperature sensing element which here takes the form of a thermocouple 58. This thermocouple is preferably exposed to the sample gas stream by mounting it in a longitudinal hole 60 in electrode holder 20. The leads of thermocouple 58 may then be conveniently located in the conductor bundle 62 which connects terminal posts 36 and 44 to an external source of polarizing potential, not shown. The advantage of locating thermocouple 58 in hole 60 through cell holder 20 is that cell 30 may be serviced or exchanged without disturbing thermocouple 58.

To the end that the pressure inside of electrolytic cell 30 may be maintained substantially equal to the external pressure applied to membrane 50, there is provided a pressure compensation passage 70 which, in the present embodiment, includes a first end section 70a which here takes the form of a longitudinal hole through the side wall of cell 30, a second end section 70c which here takes the form of a length of tubing which passes through an air tight opening in the end plate 48, a middle section 70b which here takes the form of a coil of tubing that joins passage sections 70a and 70c, and a movable fluid plug or seal 76 that is held in passage 70 by capillary action and/or surface tension. Tubing segment 70b may consist of any suitable elastomeric material such as silicone rubber or nylon. Fluid seal 76 may consist of any suitable liquid such a mineral oil which is inert to and immiscible in the electrolyte of cell 30 and which does not react chemically with or support the diffusion of sample gas. Thus, plug 76 serves as an inert, movable barrier located within passage 70.

In the embodiment and condition depicted in FIG. 1 both the interior of cell 30 and the portion of passage 70 which is between cell 30 and seal 76 are filled with electrolyte. This condition corresponds to the condition in which the electrolyte is at its maximum permissible temperature and therefore occupies the maximum permissible volume within cell 30 and passage 70. This extreme condition is reflected by the fact that fluid seal 76 occupies its outermost position in passage 70. It will be understood, however, that passage 70 may be made sufficiently long that the outermost position of seal 76 may be located in a more interior position in the passage to provide a safety margin for out-of-limits temperature excursions.

If under the above conditions the temperature within cell 30 should fall, the volume occupied by the electrolyte will decrease, causing electrolyte to be drawn into cell 30 from passage 70. As this occurs, the resulting vacuum will cause movable seal 76 to be drawn further into passage 70 by an amount proportional to the decrease in electrolyte volume. This contraction will continue as the temperature continues to fall toward its minimum permissible value, causing movable seal 76 to be drawn through the entire length of end section 70a of passage 70, the entire length of the middle section of passage 70 and into end section 70c. The only limit on this movement is the requirement that movable plug 76 not move beyond the end of end section 70c when the volume of the electrolyte attains its minimum permissible temperature and volume. It will be understood that for each position of movable seal 76 within passage 70, seal 76 prevents the electrolyte from contacting the sample gas and vice versa.

From the foregoing it will be seen that the pressure changes that would normally accompany the thermal expansion and contraction of a liquid in a filled, sealed vessel have no effect on the internal pressure of cell 30, these expansions and contractions being converted to pressure relieving movements of electrolyte into and out of the compensation passage and the associated movement of fluid plug 76. This compensatory movement is not significantly affected by the thermal expansion and contraction of the component parts of cell 30 or of passage 70 since such effects merely produce small additional changes in the position of plug 76 and since plug 76 accomplishes its intended purpose in any of its possible positions within passage 70.

In addition to providing the above described thermal pressure relief, passage 70 and plug 76 also provide a path through which the pressure inside and outside of cell 30 is equalized. This is because the electrolyte and fluid plug within the passage act as a pressure transmitting medium to passively and substantially instantaneously transmit the pressure of the sample gas to the interior of cell 30, without regard to the position of fluid plug 76 within passage 70. Since this causes pressure inside and outside of cell 30 to remain equal, there is no tendency for membrane 50 to become distorted and thereby cause erroneous outputs from cell 30. Thus, passage 70 provides pressure compensation as well as the previously described temperature compensation.

In the embodiment of FIG. 1 the entire length of passage 70 is available as a reservoir to receive fluid from or supply fluid to cell 30. In addition to this storage function, first end section 70a of passage 70 connects the outermost (sample) end of the passage to the middle portion 70b of passage 70, and second end section 70c connects the innermost (cell) end of passage 70 to the middle portion 70b of passage 70. In principle, however, there is no fundamental reason why passage 70 need be subdivided into end and middle sections. Thus, the fact that end section 70a is a hole while end section 70c is a tube is a matter of practical design convenience and not a reflection of an necessary structural relationship.

Figure 2:
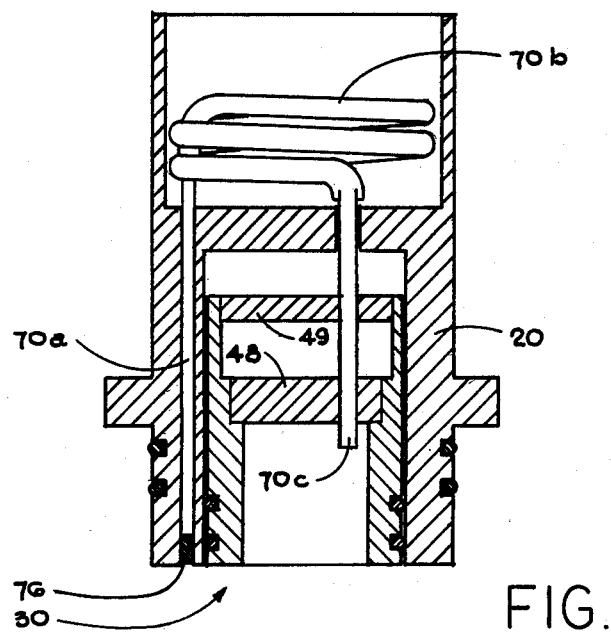
FIGS. 2 and 3 are simplified fragmentary cross-sectional views of second and third embodiments of the invention wherein those portions of the electrode assembly which are not directly involved in thermal or pressure compensation have been left out for the sake of clarity.

While, as shown in FIG. 1, passage 70 is confined to the interior of cell 30, there is no important reason why it must be so confined. An embodiment in which compensating passage 70 is all but entirely exterior to cell 30 is shown, for example, in FIG. 2. In FIG. 2 the interior detail of the electrolytic cell has been eliminated to more clearly show the structure and position of passage 70. In addition, housing sections 10 and 12 have been left out since these do not relate to the subject matter that will now be described.

Referring to FIG. 2, it will be observed that first end section 70a of passage 70 has been relocated from the side wall of electrolytic cell 30 to the side wall of electrode holder 20. End section 70a may, for example, be an additional hole of the type shown in connection with thermocouple 58 in FIG. 1. In addition, middle section 70b of passage 70 has been relocated from its position between the upper end plates 48 and 49 of electrolytic cell 30 to a position within the open upper cavity of electrode holder 20. Finally, end section 70c of passage 70 has been extended upwardly through end plates 48 and 49 to connect cell 30 to the middle section 70b of passage 70, this connection being made in the open upper cavity of electrode holder 20.

The advantages of the embodiment of FIG. 2 are, firstly, that middle section 70b of passage 70 is located in a region where more space is available and may, as a result, be made as long (and therefore as voluminous) as is required to provide thermal and pressure compensation to cell 30. In addition, the embodiment of FIG. 2 is more suitable for use in retrofit applications. This is because, in the embodiment of FIG. 2, electrolytic cell 30 may be a cell of the type that existed prior to the present invention in which a tube 70c is inserted through an end hole that is drilled through end plates 48 and 49 for that purpose.

Operationally speaking, the compensated electrode of FIG. 2 operates in the same manner as the electrode described in connection with FIG. 1. More particularly, passage 70 serves as a variable volume reservoir for absorbing from or supplying to cell 30 as much or as little fluid as is necessary to maintain pressure relief from thermal expansion and contraction, and serves as a pressure transmitting path for maintaining pressure equilibrium between the interior and exterior of the cell. In addition, fluid barrier 76 assumes, within passage 70, any position necessary to maintain the desired separation between the fluids inside and outside cell 30.

Figure 3:
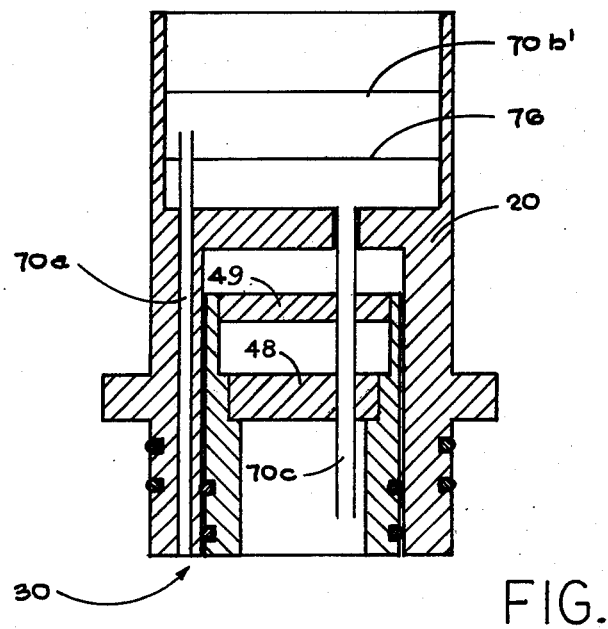

In the event that the volume of fluid to be received from or supplied to cell 30 is so large that the use of a coil such as 70b is impractical, the present invention may be practiced by use of the embodiment shown in FIG. 3. In FIG. 3 the middle section 70b of passage 70 has been replaced by a tank 70b' having any convenient shape that will fit within electrode housing 20. Tank 70b' may, for example, have an annular shape, which provides adequate interior clearance for terminal posts 36 and 44. In the preferred form of the embodiment of FIG. 3 tank 70b' will have an upper, gas filled region exposed to passage section 70a and lower, electrolyte filled region exposed to passage section 70c, the two regions being separated by floating seal 76. As a result, in FIG. 3 the pressure transmitting medium of passage 70 is in part a gas and in part a liquid.

In addition to being able to absorb or supply substantial quantities of fluids, the tank embodiment of FIG. 3 provides the advantage that liquid seal 76 is effectively confined to the middle section of passage 70. As a result there is no possibility that seal 76 can be drawn out of tube 70a or forced into tube 70c, even if cell 30 should be exposed to excessive temperature or pressure excursions or even a complete vacuumn. In all operational respects, however, the embodiment of FIG. 3 operates in the manner described in connection with FIGS. 1 and 2. It will be understood that reservoir 70b' may be located between end plates 48 and 49 of cell 30 (in the manner shown in connection with coil section 70b of FIG. 1) if it should prove desirable to confine the compensating mechanism of the invention to the interior of cell 30.

In each of the previously described embodiments, electrolytic cell 30 is of the type that is completely filled with electrolyte. The practice of the invention is not limited to electrolytic cells of the completely filled type, however, although completely filled types are preferred. In the embodiments of the invention shown in FIGS. 4a–4e, for example, there are shown electrode assemblies in which cell 30 and/or compensating passage 70 contains a gas.

Figure 4A:
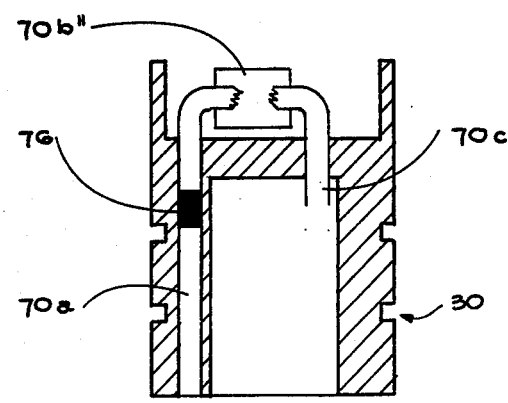
FIGS. 4a–4e are further simplified fragmentary cross-sectional views of additional embodiments of the present invention.

Referring to FIG. 4a, there is shown an embodiment of the invention in which cell 30 is partly filled with electrolyte and partly filled with a gas such as air, and in which compensating passage 70 is filled with gas on both sides of movable seal 76. In FIG. 4a, the middle section 70b of passage 70 is illustrated as a block 70b" which represents in general form a coil of the type shown in FIGS. 1 and 2, or a gas filled tank of the type shown in FIG. 3, or in general any other structure having the necessary volume and sealability.

In operation, the embodiment of FIG. 4a operates in generally the same manner as described in connection with the embodiment of FIG. 1. The fact that the fluid in passage 70 is a compressible gas rather than an incompressible liquid does not change the previously described operation of the invention. Passage 70 still receives fluid from or supplies fluid to cell 30 as required to provide relief from the pressures incident to thermal expansions and contractions of the contents of cell 30, and serves as a pressure transmission path by means of which the internal and external cell pressures are equalized. In the embodiment of FIG. 4a, however, fluid plug 76 must travel a greater distance within passage 70 for a given change in temperature and/or pressure than is the case in FIG. 1. Accordingly, for a given internal volume of passage 70, only a narrower range of temperatures and/or pressures may be accommodated.

Figure 4B:
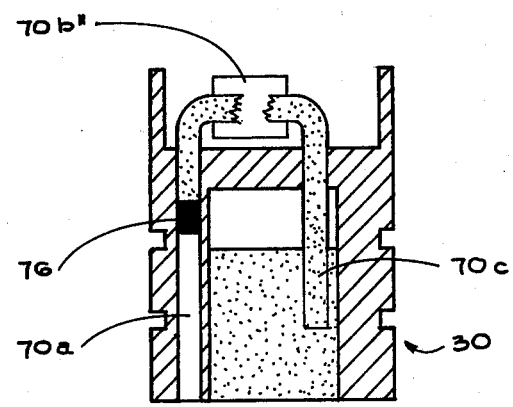

The embodiment of FIG. 4b is similar to the embodiment of FIG. 4a except that in FIG. 4b the portion of passage 70 between cell 30 and seal 76 is filled with electrolyte rather than with gas. This difference is realized by extending end section 70c of passage 70 to a point below the level of the electrolyte in cell 30. With the use of the configuration of FIG. 4b, the movements of plug 76 occur substantially only in response to pressure and temperature related expansions and contractions of the fluids within cell 30, the effect of the thermal expansion and contraction of the electrolyte in passage 70 being negligible. It will be understood that the embodiment of FIG. 4b operates in the manner described previously in connection with FIGS. 1 through 4a to provide relief from the pressures incident to thermal expansion and contraction as well as a path for equalizing pressure transmission between the interior and exterior of cell 30.

Figure 4C:
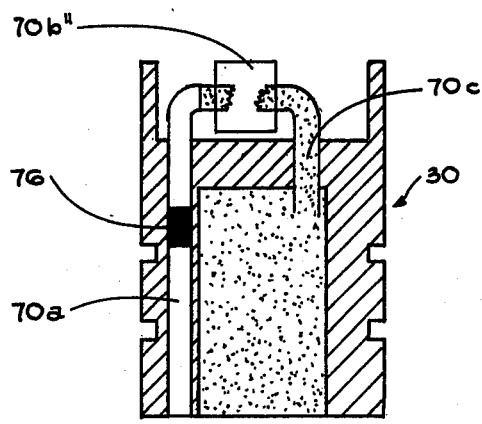
Figure 4D:
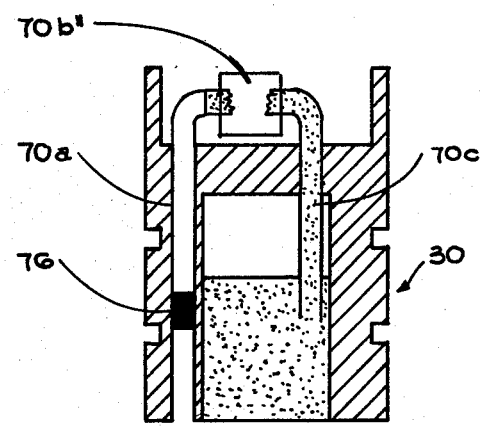

Still other embodiments of the present invention are illustrated in FIGS. 4c and 4d. In FIG. 4c cell 30 is completely filled with electrolyte and passage 70 is partly filled with electrolyte and partly filled with gas. In FIG. 4d cell 30 is partly filled with electrolyte and partly filled with gas and passage 70 is partly filled with liquid and partly filled with gas. Both of these embodiments represent hybrids of the previously described embodiments and are included primarily for the sake of completeness. It will be understood that both the embodiment of FIG. 4c and the embodiment of FIG. 4d operate in the manner described previously to provide relief from the pressures incident to thermal expansion and contraction and a path for equalizing pressure transmission between the interior and exterior of cell 30.

Figure 4E:
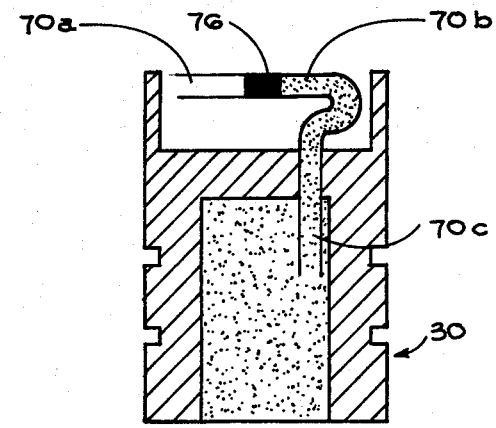

In the event that the electrode assembly of the invention is used in an environment in which it is known that the pressure of the sample gas will be substantially at atmospheric pressure, it is unnecessary for the end of end section 70a of passage 70 to be located in the vicinity of membrane 50. This is because atmospheric pressure is equally available at any point that is open to the atmosphere. In this event the invention may be practiced by means of the embodiment shown in FIG. 4e. Referring to FIG. 4e, it will be seen that cell 30 is filled with electrolyte and that the portion of passage 70 between cell 30 and plug 76 is filled with electrolyte. The end section 70a of passage 70, however, is simply open to the pressure of the atmosphere. With this arrangement, it will be seen that electrolyte may flow from cell 30 to passage 70 or vice versa as necessary to provide relief from pressures incident to thermal expansion and contraction. The internal pressure of cell 30 will be maintained substantially at atmospheric pressure by means of the pressure communicated to the interior of cell 30 through passage 70. As a result, the embodiment of FIG. 4e operates in the manner described previously in connection with FIGS. 1 through 4d and may, therefore, be used with the coil and tank structures shown in connection therewith.

While the present invention has been described in relation to a number of different embodiments, still further embodiments of the invention are possible and, accordingly, the true scope of the present invention should be determined with reference to the following claims.

What is claimed is:

1. In a gas sensor having an electrolytic cell including a housing, first and second electrodes and a gas permeable membrane, the improvement comprising:
   (a) a passage for receiving fluid from the cell and for supplying fluid to the cell to equalize the pressures inside and outside of the cell;
   (b) a first end section of said passage serving to connect said passage to a source of pressure outside of the cell;
   (c) a second end section of said passage serving to connect said passage to the inside of the cell;
   (d) a movable fluid plug located in said passage to prevent fluids external to said plug from entering said cell, said plug moving within the passage until the pressures on the inner and outer surfaces thereof are equal to one another.

2. A gas sensor as set forth in claim 1 in which said passage includes a coil of tubing inside of the housing.

3. A gas sensor as set forth in claim 1 in which said passage includes a coil of tubing outside of the housing.

4. A gas sensor as set forth in claim 1 in which said passage includes a tank inside of the housing.

5. A gas sensor as set forth in claim 1 in which said passage includes a tank outside of the housing.

6. A gas sensor as set forth in claim 1 in which said fluid plug is a layer of liquid which is immiscible in the electrolytic fluid used in said cell.

7. A gas sensor as set forth in claim 1 in which both said cell and the portion of said passage between said cell and said fluid plug is filled with an electrolytic fluid.

8. A gas sensor as set forth in claim 1 in which said first end section connects said passage to a source of sample gas.

9. A gas sensor as set forth in claim 1 in which said first end section connects said passage to the atmosphere.

10. In a gas sensor having an electrolytic cell which includes a housing, first and second electrodes, and a gas permeable membrane, the improvement comprising:
   (a) a reservoir through which fluid pressure may be applied to or released from the electrolytic cell;
   (b) first duct means for connecting said reservoir to a source of pressure outside of the cell;
   (c) second duct means for connecting said reservoir to the inside of the cell; and
   (d) a movable fluid barrier located in the path defined by said duct means and said reservoir to separate fluid inside of the cell from fluid outside of the cell, said barrier moving within the path until the pressures on opposite surfaces thereof are equal to one another, the movement of the barrier being accompanied by a flow of fluid between the inside of the cell and the portion of said path internal to the barrier.

11. A gas sensor as set forth in claim 10 in which said reservoir is a coil of tubing inside of the housing.

12. A gas sensor as set forth in claim 10 in which said reservoir is a coil of tubing outside of the housing.

13. A gas sensor as set forth in claim 10 in which said reservoir is a tank located inside of the housing.

14. A gas sensor as set forth in claim 10 in which said reservoir is a tank located outside of the housing.

15. A gas sensor as set forth in claim 13 or 14 in which said reservoir has a gas containing region and a liquid containing region.

16. A gas sensor as set forth in claim 15 in which said first duct means is a tube extending into the gas containing region of said tank, in which said second duct means is a tube extending from said cell to the liquid containing region of said tank, and in which said movable fluid barrier is a layer of liquid separating the gas and liquid containing regions of said tank.

17. A gas sensor as set forth in claim 10 in which said first duct means connects said reservoir to a source of sample gas.

18. A gas sensor as set forth in claim 10 in which said first duct means connects said reservoir to the atmosphere.

19. A gas sensor as set forth in claim 10 in which said cell is filled with an electrolyte and in which said electrolyte fills the portion of said reservoir between said cell and said fluid barrier.

20. In a gas sensor having an electrolytic cell including a housing, first and second electrodes and a gas permeable membrane, the improvement comprising:
 (a) a passage connecting the inside and outside of the cell, said passage serving to convey a flow of fluid to and from the inside of the cell, and,
 (b) a movable fluid seal located in said passage to prevent fluids from outside of the cell from entering the cell, said fluid seal moving within the passage until the pressures on the inner and outer surfaces thereof are equal to one another and thereby equalizing the pressures inside and outside of the cell.

21. A gas sensor as set forth in claim 20 wherein said passage has a volume sufficient to receive and hold any fluids expelled from said cell as a result of the thermal expansion of the cell and its contents.

22. A gas sensor as set forth in claim 20 wherein said fluid seal consists of a fluid of the type which does not appreciably wet the inside surface of said passage.

23. A gas sensor as set forth in claim 20 in which said fluid seal consists of a fluid which is immiscible in the electrolytic fluid used in said cell.

24. A gas sensor as set forth in claim 20 in which said passage includes a coil of tubing.

25. A gas sensor as set forth in claim 20 in which said passage includes a tank.

26. A gas sensor as set forth in claim 20 in which the passage connects the inside of the cell to the atmosphere.

27. A gas sensor as set forth in claim 20 in which the passage connects the inside of the cell to a source of sample gas.

* * * * *